United States Patent
Ali et al.

(10) Patent No.: US 9,597,444 B2
(45) Date of Patent: Mar. 21, 2017

(54) SYSTEMS AND METHODS FOR DETERMINING REPLACEMENT FLUID AND PLASMA FLOW RATES FOR RED BLOOD CELL EXCHANGE PROCEDURES

(71) Applicant: Fenwal, Inc., Lake Zurich, IL (US)

(72) Inventors: Zahra R. Ali, Buffalo Grove, IL (US); David E. Stude, Barrington, IL (US)

(73) Assignee: Fenwal, Inc., Lake Zurich, IL (US)

( * ) Notice: Subject to any disclaimer, the term of this patent is extended or adjusted under 35 U.S.C. 154(b) by 183 days.

(21) Appl. No.: 14/274,982

(22) Filed: May 12, 2014

(65) Prior Publication Data

US 2015/0320925 A1  Nov. 12, 2015

(51) Int. Cl.

| G01N 33/48 | (2006.01) |
|---|---|
| G01N 33/50 | (2006.01) |
| A61M 1/38 | (2006.01) |
| G06F 19/00 | (2011.01) |
| G06F 17/10 | (2006.01) |
| G06F 17/11 | (2006.01) |
| A61M 1/34 | (2006.01) |
| A61M 1/36 | (2006.01) |
| G06F 19/12 | (2011.01) |

(52) U.S. Cl.
CPC .............. *A61M 1/38* (2013.01); *A61M 1/342* (2013.01); *A61M 1/3496* (2013.01); *A61M 1/3609* (2014.02); *G06F 17/10* (2013.01); *G06F 17/11* (2013.01); *G06F 19/34* (2013.01); *A61M 1/3693* (2013.01); *A61M 2202/0429* (2013.01); *A61M 2205/3334* (2013.01); *A61M 2205/3379* (2013.01); *A61M 2205/50* (2013.01); *A61M 2230/207* (2013.01); *G06F 19/12* (2013.01)

(58) Field of Classification Search
None
See application file for complete search history.

(56) References Cited

U.S. PATENT DOCUMENTS

| 5,868,696 | A | 2/1999 | Giesler et al. |
|---|---|---|---|
| 6,027,657 | A | 2/2000 | Min et al. |
| 6,451,203 | B2 | 9/2002 | Brown |
| 6,802,982 | B2 | 10/2004 | Brown |
| 2004/0249332 | A1 | 12/2004 | Bainbridge et al. |

(Continued)

OTHER PUBLICATIONS

Extended European Search Report for European Patent Appl'n. No. EP 15 16 6708, dated Oct. 1, 2015.

(Continued)

*Primary Examiner* — Russell S Negin
(74) *Attorney, Agent, or Firm* — Cook Alex, Ltd.

(57) ABSTRACT

Systems and methods for performing a red blood cell exchange procedure are disclosed. In one aspect, the flow rates of a replacement fluid (e.g., red blood cells from a healthy donor) and plasma being flowed to a blood source are calculated based on certain parameters of the procedure that are known, including the flow rate of blood being drawn from the source and the volume of replacement fluid to be used during the procedure. The replacement fluid flow rate and the plasma flow rate are calculated in a way that allows for simultaneous depletion of the supply of replacement fluid and achievement of another prescribed process parameter. The other prescribed process parameter depends on the nature of the procedure, namely whether the fluid volume and hematocrit of the source are to change by the end of the procedure or remain the same.

20 Claims, 4 Drawing Sheets

(56) References Cited

U.S. PATENT DOCUMENTS

2009/0211987 A1  8/2009  Min
2010/0168639 A1  7/2010  Cantu et al.
2013/0267884 A1  10/2013  Boggs et al.

OTHER PUBLICATIONS

Cobe Spectra Apheresis System, Therapeutic Apheresis Guide, Red Blood Cell Exchange (RBCX) Procedure, pp. 4-1 through 4-21.

SYSTEMS AND METHODS FOR DETERMINING REPLACEMENT FLUID AND PLASMA FLOW RATES FOR RED BLOOD CELL EXCHANGE PROCEDURES

FIELD OF THE DISCLOSURE

The present disclosure is directed to the processing and collection of blood and its components. More particularly, the present disclosure is directed to methods and systems for red blood cell exchange, in which blood is drawn from a subject, the red blood cells are separated from the other blood components, and then the other blood components are returned to the subject, along with one or more replacement fluids.

DESCRIPTION OF RELATED ART

Blood processing systems and methods that relate to a therapeutic exchange procedure typically withdraw a biological fluid, such as whole blood, from a subject or source (e.g., a donor or patient or container). The biological fluid, such as whole blood, may be directed to a separator, such as a centrifugal or membrane assembly, for separation of at least one constituent component, such as at least one blood component, for example, red blood cells, plasma, and/or platelets, from the remaining blood components. Depending on the procedure, certain separated constituent components may be retained by the system and not returned to the source. The remaining separated constituent components may be returned to the source together with one or more fluids to replace the constituent retained by the system. The particular separated constituent that is not returned to the donor may depend on the specific medical needs of the source. For example, one type of therapeutic exchange procedure is a red blood cell exchange procedure that removes a quantity of separated red blood cells from the withdrawn whole blood of a source and returns to the source at least one replacement fluid, such as red blood cells from a healthy donor, containing an additive solution or other fluid, along with the remaining separated blood components.

In a therapeutic exchange procedure, it is generally desired to achieve a certain target fraction of original source cells remaining (referred to herein as "FCR") in order to reduce the population of diseased cells. It may also be desired to maintain a source's fluid volume such that the difference between the volume of removed fluid and replaced fluid, $\Delta V$, is within a desired range. In a red blood cell exchange procedure it may also be desired to achieve a targeted volume fraction of red blood cells (fractional hematocrit, $H_{TF}$) at the conclusion of the procedure so as to avoid the source receiving too many or too few replacement red blood cells. A system and method for controlling hematocrit during a therapeutic red blood cell exchange procedure utilizing a hematocrit sensor is disclosed in U.S. Patent Application Publication No. 2009/0211987, which is incorporated herein by reference. Systems and methods for achieving a target FCR, hematocrit, and fluid volume change during a therapeutic red blood cell exchange procedure, as well as systems and methods for performing such a procedure with iso-volemic (i.e., without any change in volume) hemodilution, are disclosed in U.S. Patent Application Publication No. 2013/0267884, which is incorporated herein by reference.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood processing system is provided. The system includes a blood separation device configured to separate whole blood from a blood source into a first component including separated red blood cells and a second component including separated plasma. An inlet pump is operable to convey whole blood from the blood source into the blood separation device at a prescribed rate $Q_3$. A plasma pump is operable to convey separated plasma from the blood separation device to the blood source at a plasma flow rate. A replacement fluid pump is operable to convey a replacement fluid to the source at a replacement fluid flow rate. A controller is programmed to calculate the plasma flow rate and the replacement fluid flow rate based at least in part on $Q_3$ and a volume $V_R$ of replacement fluid to be flowed to the source. The controller adjusts the operation of the replacement fluid pump to achieve the calculated replacement fluid flow rate, while adjusting the operation of the plasma pump to achieve the calculated plasma flow rate. The plasma flow rate and the replacement fluid flow rate are calculated so as to simultaneously deplete the volume $V_R$ of replacement fluid and achieve one other prescribed process parameter. The prescribed process parameter is either maintaining a hematocrit and a fluid volume of the source at constant levels, maintaining the hematocrit of the source at a constant level while changing the fluid volume of the source from an initial level to a prescribed level, maintaining the fluid volume of the source at a constant level while changing the hematocrit of the source from an initial level to a prescribed level, or changing the hematocrit and the fluid volume of the source from initial levels to prescribed levels.

In another aspect, a method is provided for performing a red blood cell exchange procedure. The method includes calculating a replacement fluid flow rate and a plasma flow rate. Whole blood is drawn from a source at a prescribed rate $Q_3$, with the whole blood being separated into a first component including separated red blood cells and a second component including separated plasma. A replacement fluid is flowed to the source at the replacement fluid flow rate and separated plasma is flowed to the source at the plasma flow rate. The replacement fluid flow rate and the plasma flow rate are calculated based at least in part on $Q_3$ and a volume $V_R$ of replacement fluid to be flowed to the source. The rates are also calculated so as to simultaneously deplete the volume $V_R$ of replacement fluid and achieve one other prescribed process parameter. The prescribed process parameter is either maintaining a hematocrit and a fluid volume of the source at constant levels, maintaining the hematocrit of the source at a constant level while changing the fluid volume of the source from an initial level to a prescribed level, maintaining the fluid volume of the source at a constant level while changing the hematocrit of the source from an initial level to a prescribed level, or changing the hematocrit and the fluid volume of the source from initial levels to prescribed levels.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Known systems of the type described in U.S. Patent Application Publication No. 2013/0267884 (which was incorporated by reference above), determine one or more process parameters for a red blood cell exchange procedure based at least in part upon a target FCR. However, in some cases, a target FCR is not available, whereas other information, namely the volume of replacement fluid to be used and the rate at which blood is to be drawn from the source, are known. In systems and methods according to the present disclosure, selected process parameters (such as replacement fluid and plasma flow rates) may be calculated based, at least in part, upon the volume of replacement fluid to be flowed to a blood source and the rate at which blood is to be drawn from the source. The systems and methods described herein permit such information and parameters to be determined for both isovolemic and non-isovolemic procedures, as well as iso- and non-iso-hematocrit procedures. As used herein, the term "isovolemic" refers to a procedure in which the fluid volume of the subject at the end of the procedure is equal to the fluid volume of the subject at the beginning of the procedure, while the term "iso-hematocrit" refers to a procedure in which the hematocrit of the subject (i.e., fluid percentage made up of red blood cells) at the end of the procedure is equal to the hematocrit of the subject at the beginning of the procedure.

Figure 1:
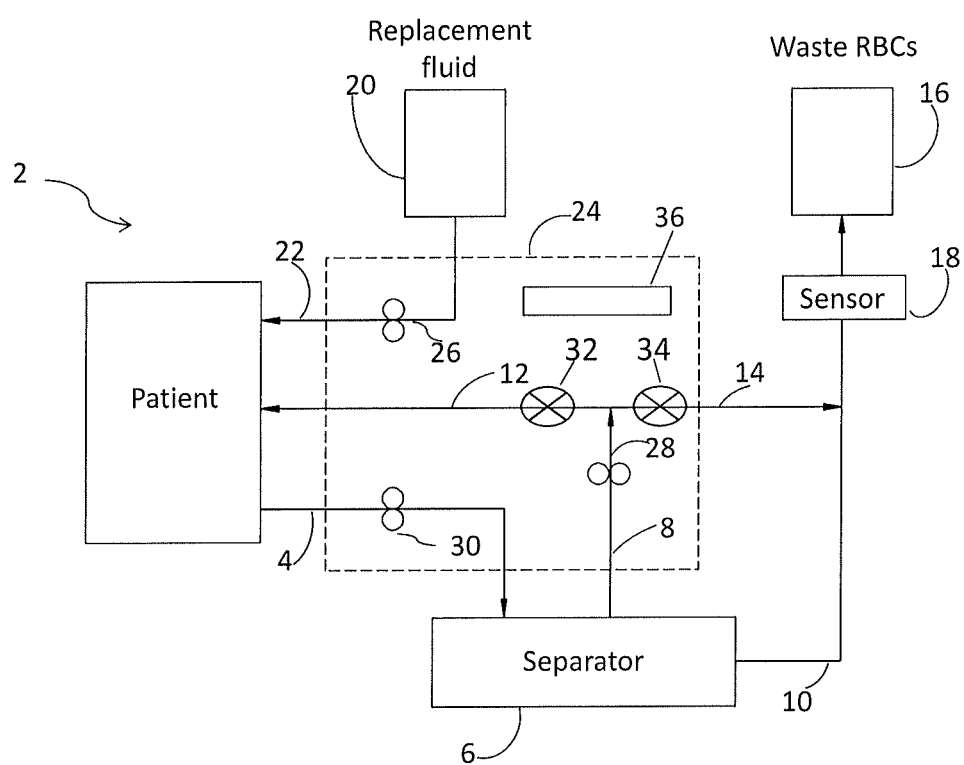
FIG. 1 is a diagrammatic view of a blood processing system in accordance with one embodiment of the subject matter described herein.

In accordance with one embodiment of the present disclosure, FIG. 1 schematically illustrates a processing system, generally indicated at 2, that may be used for processing various fluids in accordance with the subject matter described herein. The system 2 is particularly well suited for processing whole blood and/or other suspensions of biological fluids. Although the processing of whole blood will be described, the illustrated embodiments are not limited to such processing and may be employed for processing other biological fluids. By way of example and not limitation, the systems described herein are particularly suited for a therapeutic red blood cell exchange procedure during which red blood cells are separated from withdrawn whole blood and the remaining blood components and replacement red blood cells alone or with other replacement fluid(s), such as an additive solution, is returned to a source or patient. Examples of additive solutions include, but are not limited to Adsol®, Erythro-sal, SAG-M, PAGGSM, and others. It should be understood that the systems described herein are not limited to such a procedure and that other procedures are also within the scope of the present disclosure. Further, while the methods and systems described herein are presented in the context of drawing blood from and returning fluids to a living patient, it is also within the scope of the present disclosure for the blood source/fluid recipient to be a non-living entity, such as a blood bag or other container.

In FIG. 1, the system 2 includes an inlet flow path, generally indicated at 4, that communicates with a subject or donor or patient for flowing (withdrawing) at least a first fluid, such as whole blood, from the patient or source. In FIG. 1, a separator or blood separation device, generally indicated at 6, may be associated with the inlet flow path 4 for receiving the whole blood and separating the whole blood from the patient or source into one or more separated blood components. By way of example, the separator 6 may separate a first component comprising primarily red blood cells from a second component comprising plasma and the remaining blood components, e.g., plasma, platelets, and white blood cells. In FIG. 1, a first outlet or plasma flow path, generally indicated at 8, preferably communicates with the separator 6 for flowing the separated plasma and/or other remaining blood components, such as platelets and/or white blood cells, from the separator 6. A second outlet or red blood cell flow path, generally indicated at 10, preferably communicates with the separator 6 for flowing the separated red blood cells from the separator 6.

The separated plasma may flow from the separator 6 generally in two ways or along two branches of the first outlet flow path 8, such branches generally indicated at 12 and 14. A first branch 12 may communicate, either directly or indirectly with the patient and a second branch 14 may communicate with the red blood cell flow path 10 at a selected location to combine and/or mix with the separated red blood cells.

Also in FIG. 1, a first container or reservoir, generally indicated at 16, is preferably associated with the red blood cell flow path 10, such as at a downstream end of such flow path 10. The first reservoir 16 preferably communicates with the separator 6 to allow the separated red blood cells to flow from the separator 6 to such reservoir 16. A monitoring device, such as a sensor, generally indicated at 18, is optionally associated with the second outlet flow path 10 at a sensing location that is preferably downstream of the selected location where separated plasma in the plasma flow path second branch 14 and red blood cells in the second outlet flow path 10 may combine. In FIG. 1, a second reservoir, generally indicated at 20, may contain a replacement fluid, such as fresh red blood cells, and may communicate with the patient or source, either directly or indirectly, by way of a replacement fluid flow path, generally indicated at 22. While only a single reservoir containing replacement fluid is shown in FIG. 1, the system may include multiple reservoirs containing replacement fluid, as will be described in greater detail below. Although in FIG. 1, the replacement fluid flows to the patient or source separately from the separated plasma, it is also possible for the replacement fluid and separated plasma to flow by way of a combined return flow path that communicates either directly or indirectly with the patient or source. The system 2 may include additional components without departing from the scope of the present disclosure, such as a hematocrit sensor.

In FIG. 1, a controller or flow controller, generally indicated at 24, may be associated with one or more flow controlling devices, such as, for example, pumps, generally indicated at 26, 28, and 30, and valves 32 and 34 that control the flow of fluids through the various flow paths. In the illustrated embodiment, one pump 28 is associated with the plasma flow path 8 for controlling fluid flow of the separated plasma to the patient or source and to the red blood cell flow path 10. The valves 32 and 34, as operated by the flow controller 24, serve to alternately open and close the first and second branches 12 and 14 of the plasma flow path 8 to fluid flow, respectively. The valve 34 on the second branch 14 may be initially closed to prevent fluid flow therethrough, while the valve 32 associated with the first branch 12 may be open, thereby directing plasma from the separator 6 back to the patient or source. If excess plasma is directed out of the separator 6, then the valve 32 on the first branch 12 of the plasma flow path 8 may be closed and the other valve 34 on the second branch 14 opened to direct the plasma into the red blood cell flow path 10, where it flows to the waste reservoir 16. The other two pumps 26 and 30 are shown in association with the replacement fluid flow path 22 (for delivering replacement fluid to the patient or source) and with the whole blood flow path 4 (for withdrawing whole blood from the patient or source), respectively. In this configuration the pumps may be referred to as the replacement fluid pump 26, the plasma pump 28, and the inlet pump 30. Additional flow controlling devices may also be incorporated into the system 2 without departing from the scope of the present disclosure.

In FIG. 1, the flow controller 24 may include a main or system controller, generally indicated at 36, such as a programmable controller employing a programmable microprocessor, that is operatively associated with the pumps 26, 28, and 30, and the valves 32 and 34 to control the operation of the various flow controlling devices. In accordance with the present disclosure, the main controller may be programmed or configured to operate the system to simultaneously deplete the entire supply of replacement fluid while also achieving another prescribed process parameter, as will be described in greater detail herein.

Figure 2:
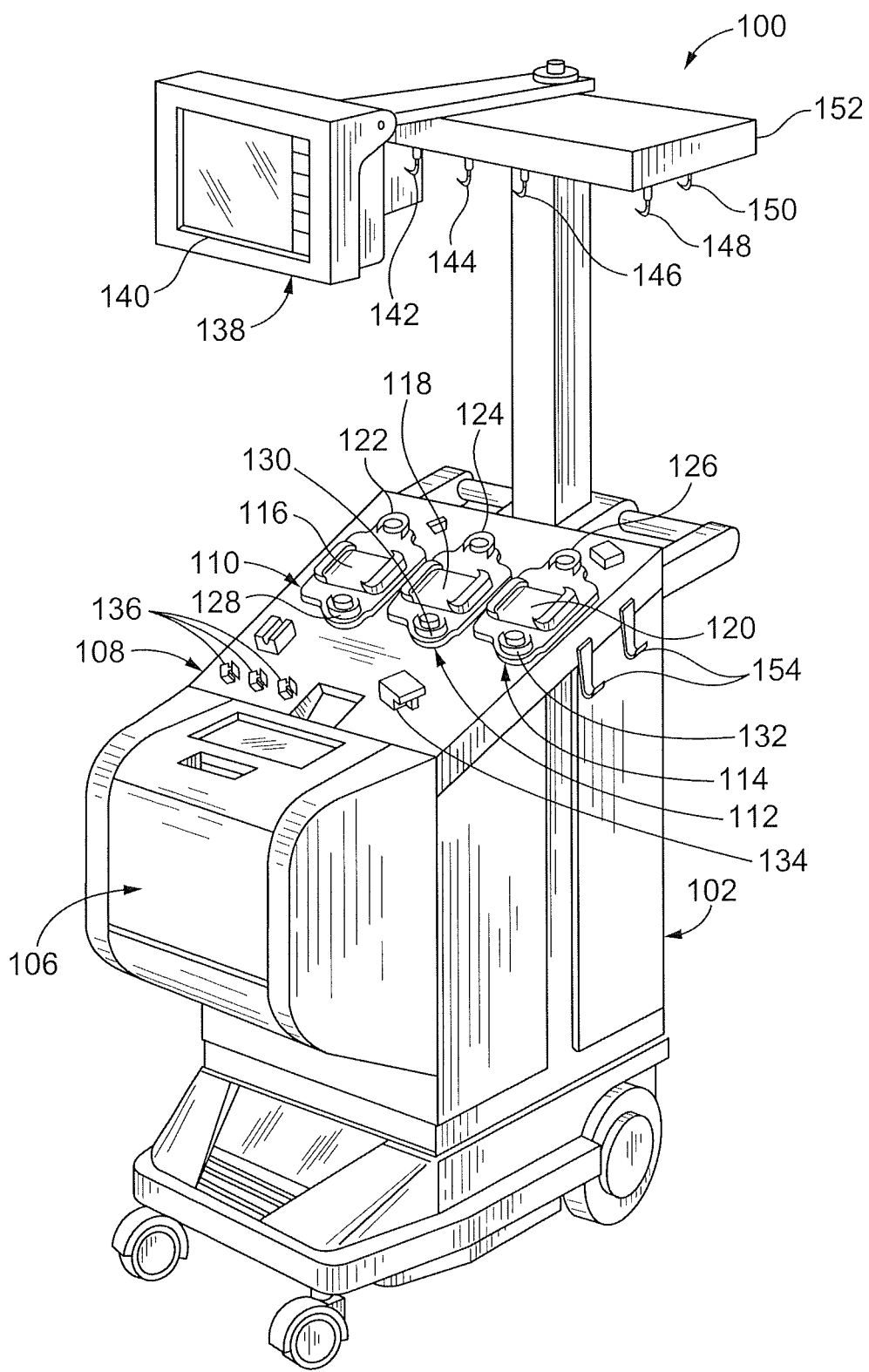
FIG. 2 is a perspective view of a reusable blood processing device that may be employed as part of or in association with the subject matter described herein.

FIG. 2 illustrates a blood processing system, generally indicated at 100, which may be understood as a particular example of a system of the type shown schematically in FIG. 1. The illustrated embodiment is substantially identical to a commercial centrifuge sold by Fenwal, Inc. as the AMICUS® separator, which is disclosed in numerous patents and patent applications, not limited to but including U.S. Pat. No. 5,868,696, which is incorporated herein by reference.

Figure 3:
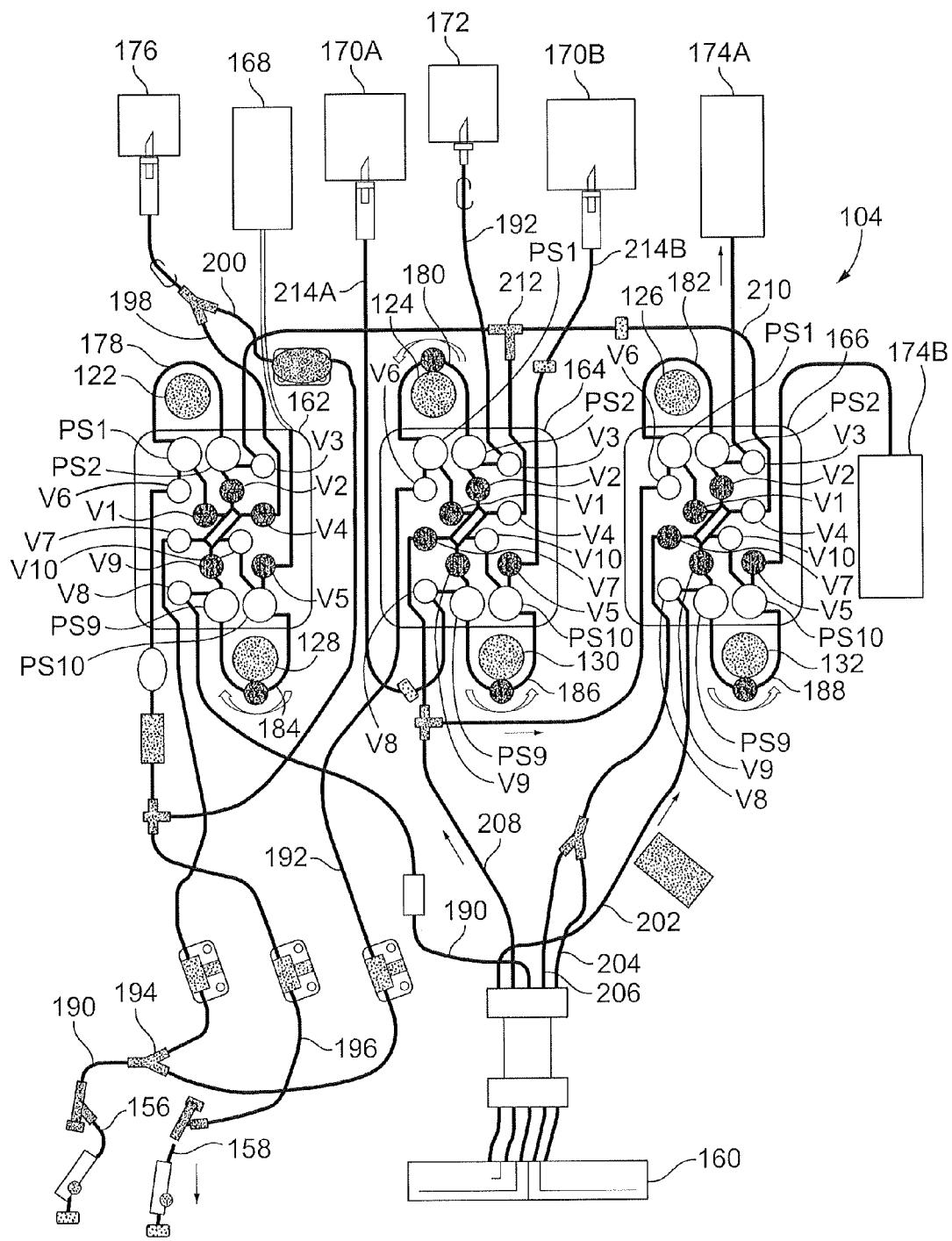
FIGS. 3 and 4 are plan views of a disposable tubing flow set for use with the blood processing device of FIG. 2, illustrating two possible flow arrangements during an exemplary therapeutic red blood cell exchange procedure.
Figure 4:
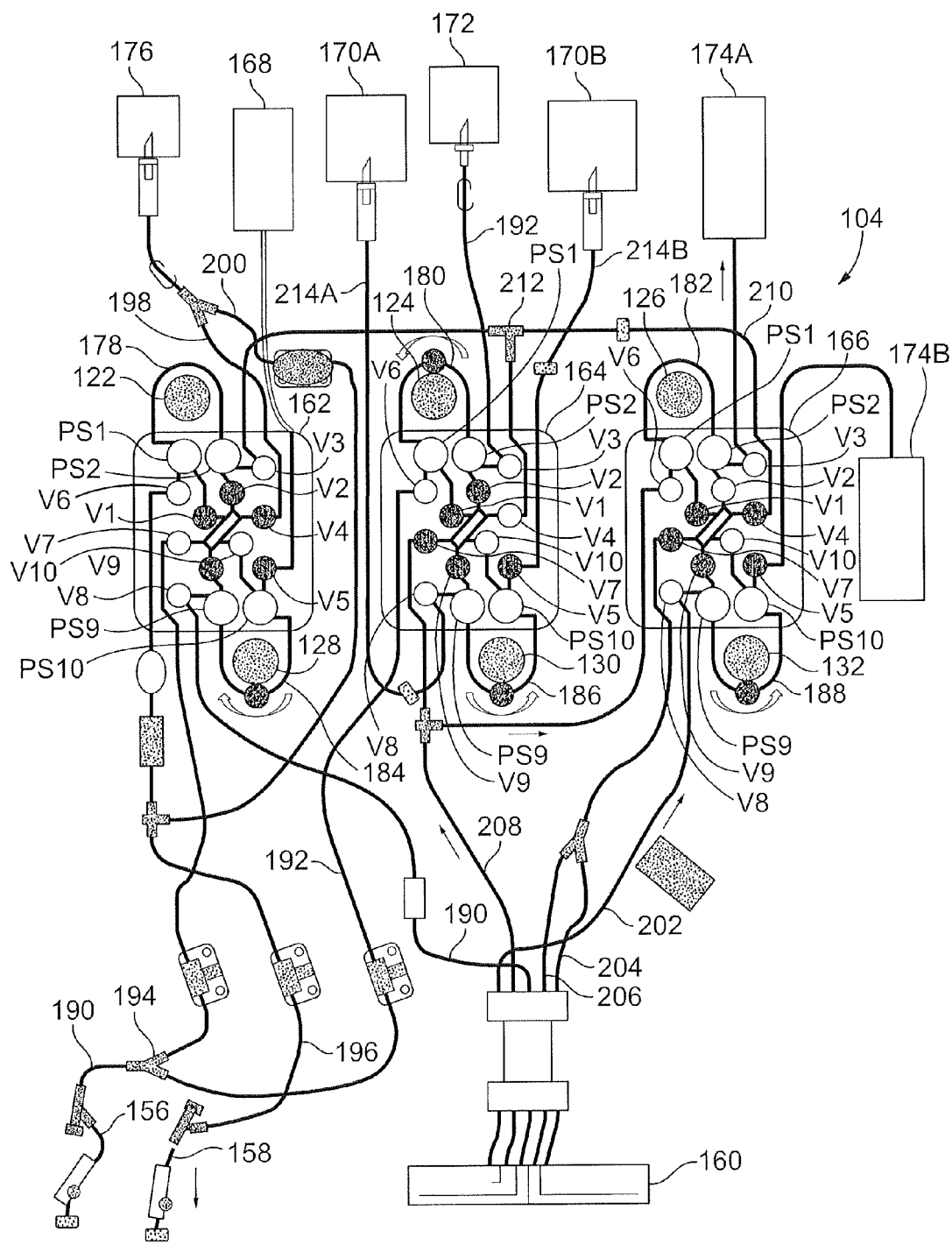

As shown in FIG. 2, the blood processing system 100 includes a separation assembly or blood separation device, specifically a centrifuge rotor assembly, generally within the housing indicated at 102, and is configured to control fluid flow through a disposable fluid processing set, which is generally indicated at 104 in FIGS. 3 and 4, used in association with the processing system 100. As noted above, the separation assembly need not be a centrifugal processing assembly, and other separation technology or devices, such as membrane separators, may also be used without departing from the scope of the present disclosure. The blood separation device 102 (which corresponds to the separator 6 of FIG. 1) receives and separates a biological fluid, such as whole blood and/or other biological fluids, into two or more constituent components. The blood processing system 100 and the blood separation device 102 are preferably adapted to be durable and reusable over a long term. The fluid processing set 104, in contrast, is disposable, and a fresh sterile set is assembled with the blood processing system 100 for each use.

In FIG. 2, the blood separation device 102 includes an access compartment, generally indicated at 106, which houses a portion of the disposable set 104, such that when the blood separation device 102 is activated, the constituent components are separated within such portion of the set 104. A panel, generally indicated at 108, provides a surface for receiving another portion of the disposable set 104. In the illustrated embodiment, the panel 108 includes three pumping and valving stations, or respective left, middle and right stations, generally indicated at 110, 112, and 114. Each station 110, 112, and 114 respectively includes a valve interface portion 116, 118, and 120, which controls the opening and closing of associated valves in a disposable flow control cassette, described in greater detail below. Each station 110, 112, and 114 also has a respective upper flow controlling device or pump 122, 124, 126 and a lower flow controlling device or pump 128, 130, 132. Each illustrated pump 122, 124, 126, 128, 130, 132 is a peristaltic pump adapted to be associated with a section of tubing of the disposable set 104 to provide flow control, although other types of pumps or other flow controlling devices, such as diaphragm pumps or gravity controlled devices are also possible. The panel 108 may further include a sensor or detector 134, such as an optical detector, and/or other sensors or clamps, generally indicated at 136, for controlling and/or monitoring fluid and/or air flow in the disposable set 104.

The illustrated blood processing system 100 further includes a main or system controller, generally indicated at 138. The controller 138 may be a programmable controller that is operable to control the system 100 for various processes, including the therapeutic red blood cell exchange procedure described in greater detail below. An operator interface module 140 may allow for viewing of the past, current, and/or upcoming operations and/or provide for operator input by way of a touch screen and/or one or more tactile controls. One or more weight scales 142, 144, 146, 148, 150 may be associated with the controller 138. Such scales may be attached to a platform or stand 152 that allows one or more fluid containers to be attached to or hung from the scales and to allow for weight measurement of such containers before, during, and/or after the processing procedure. One or more hooks 154 may also extend downwardly from a right or left side of the panel 108 to allow attachment of other fluid containers and may also be associated with a weight scale, if desired.

FIGS. 3 and 4 illustrate one possible disposable fluid flow processing set 104 that may be employed for use with the blood processing system 100 of FIG. 2 for performing a therapeutic red blood cell exchange procedure in accordance with the present disclosure. It should be understood that other paired blood processing systems and disposable sets may also be employed without departing from the scope of the present disclosure.

The illustrated disposable set 104 includes a draw tubing or flow path 156 and a return tubing or flow path 158, each having a patient/source access device, such as a needle, associated therewith. The disposable set 104 of FIGS. 3 and 4 is a double needle system, in which one needle or vein access device is used for withdrawal of fluid from a patient or source and another is used for return of fluid to the patient or source, although it should be understood that the present disclosure is not limited to double needle processing and may include single needle and other types of processing sets.

The disposable set 104 of FIGS. 3 and 4 further includes a processing chamber 160; left, middle and right pumping, flow control, and valving cassettes 162, 164, and 166; an auxiliary reservoir or container 168 for pressure relief or for diverted air; containers 170A and 170B for replacement fluids (such as saline, albumin, and/or replacement red blood cells); a container 172 for an anticoagulant; waste containers 174A and 174B for red blood cell and/or plasma waste; and a container 176 for saline. Each container may be respectively associated with a corresponding weight scale (see, e.g., weight scales 142, 144, 146, 148, and 150 of FIG. 2) for determining the amount of fluid that is removed from or added to such container. The set 104 also includes various tubing paths discussed in further detail below.

Each cassette 162, 164, and 166 may have a similar internal construction and, as such, only one cassette 162 will be described. However, it should be understood that like alpha-numeric reference characters are applicable for each cassette. The left cassette 162 includes at least one, and preferably a plurality of, pressure sensing chambers, such as PS1, PS2, PS9, and PS10, preformed fluid flow pathways, and at least one and preferably a plurality of valves, such as V1-V10. The disposable set 104 of FIGS. 3 and 4 may be used in a variety of flow arrangements, in which different fluids are transferred to different locations within the disposable set 104 based upon the orientation of the valves. For example, in a first flow arrangement (FIG. 3), the waste red blood cells exit the separator through flow path 208, pass through the right cassette 166, and up to the waste container 174A. Selected valves of the cassettes are open, while other valves are closed, to cause the plasma pump 132 to send the patient or source's plasma through flow path 210 and joins with replacement fluid at the connector indicated as 212, to be returned to the patient or source. In an alternative flow arrangement (FIG. 4), different valves are open and closed to cause the plasma pump 132 to send the patient or source's excess plasma to the waste container 174A with the patient or source's red blood cells. This second flow arrangement is only employed in the event that excess plasma is pumped from the separator and does not need to be returned to the patient or source. In the present disclosure, any reference to the plasma flow rate assumes that the plasma is being flowed from the separator back to the patient or source (e.g., using fluid path 210), along with replacement fluid, rather than being discarded or retained by the system (e.g., by being flowed to the waste container 174A).

In the modes of operation illustrated in FIGS. 3 and 4, a valve is "closed" if the circle indicating the valve in a cassette is darkened and is "open" if the circle is not darkened. The number and configuration of such chambers and valves are not limited to that shown, and other variations are also possible, including variations for the interconnecting flow paths between such chambers and valves. Each of the chambers and valves preferably is associated with a respective portion of the respective pumping and valving station 110, 112, and 114 to control the flow of fluid.

As described above, each pump 122, 124, 126, 128, 130, and 132 may be a peristaltic pump adapted to be associated with a section of tubing to provide flow control. For example, each pump 122, 124, 126, 128, 130, and 132 may be associated with a respective tubing segment or loop 178, 180, 182, 184, 186, and 188. The upper pumps 122, 124, and 126 may each be associated with two pressure sensing chambers PS1 and PS2, with one being located downstream and the other located upstream of the associated pump, depending on which direction is the desired flow direction, which direction may change, if desired, one or more times during and/or after the procedure. Similarly, the lower pumps 128, 130, and 132 each may be associated with two pressure sensing chambers PS9 and PS10 located on either upstream or downstream side thereof. Such peristaltic pumps 122, 124, 126, 128, 130, and 132 typically function by rotation of one or more outward extensions or rollers that press against the exterior of the respective tubing segment 178, 180, 182, 184, 186, and 188 to progressively compress or "push" fluid in the desired direction of flow. The pumps may be bi-directional, and in the modes of operation illustrated in FIGS. 3 and 4, the direction of rotation of the pumps, and consequently the direction of fluid flow, is indicated by an arrow.

The set 104 may further include a first flow path 190 that fluidly communicates with the draw tubing 156 for withdrawing whole blood from a patient or source. An anticoagulant flow path 192 may communicate with the first flow path 190 at a Y-branch connector 194 to allow anticoagulant to mix with the withdrawn whole blood. Anticoagulant from the anticoagulant container 172 may be pumped to the first flow path 190 by the upper or anticoagulant pump 124 of the middle cassette 164 and flow through open valves V3 and V6 of such cassette 164 to mix with the withdrawn whole blood. The set 104 may also include a return or replacement fluid flow path 196 that fluidly communicates with the return tubing 158 to allow one or more fluids, such as a replacement fluid, to flow to the patient or source. One or more saline flow paths 198 and 200 may also be in respective communication with the whole blood and return flow paths 190 and 196 to allow saline flow, if desired, before, during and/or after the procedure.

By way of example and not limitation, the withdrawn whole blood may flow into the first flow path 190 and through the left cassette 162 and the lower or whole blood pump 128 of such cassette 162. The first flow path 190 preferably communicates with the processing chamber 160 so as to allow the withdrawn whole blood from the patient to be separated into selected constituent blood components, such as red blood cells, platelets, and/or plasma.

Outlet flow paths 202 and 208 may allow separated blood components, such as red blood cells, plasma, and/or platelets, to separately exit the processing chamber 160. For example, separated red blood cells from the processing chamber 160 may flow through one of the flow paths 208 (which may be referred to as the red blood cell flow path), while separated plasma from the processing chamber 160 may flow through the other flow path 202 (which may be referred to as the plasma flow path). An optical detector, such as the optical detector 134 discussed above, may be associated with the plasma flow path 202 to assist in optical detection of blood components, e.g. platelets or red cells, in the plasma constituent.

Separated red blood cells flowing from the processing chamber 160 preferably flow through the red blood cell flow path 208 to one of the red blood cell containers 174A or 174B. In one flow arrangement, separated red blood cells may flow through the right cassette 166 before being directed into one of the waste containers 174A or 174B. As discussed above, the waste red blood cell containers 174A, 174B may also be associated with weight scales for measuring the amount of the separated red blood cells flowing into such containers during the procedure.

As described above, in different flow arrangements, the separated plasma from the processing chamber 160 flows through the plasma flow path 202 either to one of the waste containers 174A, 174B (FIG. 4) or to the patient/source (FIG. 3). For example, when the separated plasma is to be returned to the patient or source, it may flow from the processing chamber 160 through the right cassette 166 to a first passageway 210 in communication with the return flow path 196, with the separated plasma being pumped by the lower or plasma pump 132 of the right cassette 166. Separated plasma may flow into the return flow path 196 at a selected location or connector 212, which combines the plasma and replacement fluid (which is being pumped out of the replacement fluid container or containers 170A, 170B by one or more pumps, which may be designated as a replacement fluid pump or pumps) into a combined fluid stream for return to the patient or source.

Replacement fluid flows from one of the replacement fluid containers 170A, 170B to the patient or source through the return flow path 196. For example, the replacement fluid flows from either container 170A or 170B through a replacement fluid source path 214A or 214B to the middle cassette 164. The lower or replacement fluid pump 130 of the middle cassette 164 may control the flow of the replacement fluid. The replacement fluid flows into the return flow path 196 and flows to the patient or source. As noted above, separated plasma (as well as platelets and white blood cells) may be combined with the replacement fluid in a single fluid stream. The return flow path 196 may also flow through the left cassette 162 before flowing to the patient or source, in which case the combined fluid stream may also be pumped by operation of the upper or return pump 122 of the left cassette 162 to assist the return flow of fluid to the patient or source.

In a method of performing a red blood cell exchange procedure according to the present disclosure, an operator or technician enters selected process parameters using the operator interface module 140. In procedures according to the present disclosure, the blood draw rate and volume of replacement fluid to be used will be known and may be entered by the operator or automatically input by the controller 138 if the blood draw rate and/or replacement fluid volume are measured or sensed or are otherwise provided as default values. Addition information may also be entered by the operator or provided by the controller 138, including the patient or source's initial total blood volume (which may be calculated according to known methods using the source's sex, height, and weight in the case of a living source or a scale in the case of a non-living source), the hematocrits of the patient or source's blood and the replacement fluid, the targeted fluid volume change for the patient or source (in non-iso-volemic procedures), and the targeted hematocrit of the patient or source's blood (in non-iso-hematocrit procedures).

Based on the entered information, the system controller 138 may calculate or determine the other required process parameters (e.g., the flow rates of the replacement fluid and separated plasma flowed to the patient or source) and then command the other components of the blood processing system 100 to carry out the procedure. The equations used by the controller 138 to calculate the unknown process parameters may vary depending on the nature of the procedure to be performed (namely, whether the procedure is an iso-hematocrit or a non-iso-hematocrit procedure and whether the procedure is a iso-volemic or non-iso-volemic procedure), so the operator interface module 140 may prompt an operator to input the nature of the procedure prior to calculating the process parameters. The decision to change volume or hematocrit or to maintain a subject at its current levels may be based on any of a number of factors. Frequently, a doctor or health care professional will choose to maintain a subject at its current volume and current hematocrit, but there are circumstances in which changing volume and/or hematocrit are advantageous. For example, if the red blood cell volume of a subject is depleted prior to exchange (e.g., due to a secondary condition or for procedure efficiency), then a non-iso-hematocrit exchange procedure may be selected to raise the hematocrit of the subject to a normal level or some other desired value. In another example, if the subject is a human patient with a secondary condition (e.g., anemia, hypertension, congestive heart failure, etc.), the exchange procedure may be selected so as to treat the secondary condition as well by using any combination of a non-iso-volemic, non-iso-hematocrit exchange procedure.

Iso-Hematocrit, Iso-Volemic Procedures

For an iso-hematocrit, iso-volemic procedure, the target patient/source hematocrit and volume are equal to the initial hematocrit and volume of the patient or source. Thus, the replacement fluid and plasma flow rates are to be calculated in a way that allows for simultaneous depletion of the supply of replacement fluid and maintenance of the hematocrit and fluid volume of the patient or source at constant levels.

Typically, the equation used to relate the time required to achieve a target hematocrit to the replacement fluid and plasma flow rates is:

$$t_{HF} = -\frac{V_0}{Q_1 + Q_5}\ln(Z), \tag{1}$$

where $t_{HF}$ is the time required to achieve the target hematocrit for an iso-volemic procedure, $V_0$ is the initial volume of the patient or source's blood, $Q_1$ is the replacement fluid flow rate, $Q_5$ is the plasma flow rate (i.e., the rate at which plasma separated from the patient or source's blood is returned to the patient or source), and $$Z = \frac{H_{T1} - FH_{TF}}{H_{T1} - FH_{T0}}, \tag{2}$$

where $H_{T1}$ is the hematocrit of the replacement fluid, $H_{TF}$ is the target hematocrit, $H_{T0}$ is the initial hematocrit of the patient or source's blood, and $$F = \frac{Q_1 + Q_5}{Q_1}. \tag{3}$$

Equations (1), (2), and (3) may be found in U.S. Patent Application Publication No. 2013/0267884, which was incorporated by reference above.

For iso-hematocrit, iso-volemic procedures, the time required to reach the target hematocrit ($t_{HF}$) is zero, and equation (1) cannot be used to determine the appropriate replacement fluid and plasma flow rates. Accordingly, the appropriate replacement fluid and plasma flow rates must be determined in a different way.

To keep the patient or source's hematocrit constant and deplete the specified replacement fluid volume, the replacement fluid may be flowed to the patient or source at a rate ($Q_1$) that is proportional to the rate at which blood is drawn from the patient or source ($Q_3$), such that the hematocrit of the patient or source is maintained throughout the procedure by the replacement fluid and plasma being flowed to the patient or source. This relationship may be modeled by the following equation:

$$H_{T0} = \frac{Q_1}{Q_1 + Q_5} H_{T1}, \quad (4)$$

with the replacement fluid and plasma being returned to the patient or source at the calculated rates until the supply of replacement fluid allotted for the procedure has been depleted.

In an iso-volemic procedure:

$$Q_1 + Q_5 = Q_3 \quad (5),$$

such that equation (4) may be rewritten as:

$$H_{T0} = \frac{Q_1}{Q_3} H_{T1}, \quad (6)$$

which may be rearranged to solve for $Q_1$:

$$Q_1 = \frac{H_{T0}}{H_{T1}} Q_3. \quad (7)$$

Rearranging equation (5) to isolate $Q_5$ yields:

$$Q_5 = Q_3 - Q_1. \quad (8)$$

Thus, equations (7) and (8) may be used by the system controller 138 to calculate proper replacement fluid and plasma flow rates for iso-hematocrit, iso-volemic procedures in which the blood draw rate and replacement fluid volume (along with the hematocrits of the patient or source's blood and the replacement fluid) are known.

Iso-Hematocrit, Non-Iso-Volemic Procedures

For an iso-hematocrit, non-iso-volemic procedure, the target patient or source hematocrit is equal to the initial hematocrit of the patient or source, but the patient volume changes. Thus, the replacement fluid and plasma flow rates are to be calculated in a way that allows for simultaneous depletion of the supply of replacement fluid while maintaining the hematocrit of the patient or source at a constant level and changing the fluid volume of the patient or source from an initial level to a target level.

Typically, the equation used to relate the time required to achieve a target hematocrit to the replacement fluid and plasma flow rates is:

$$t_{HF} = \frac{V_0}{Q_1 + Q_5 - Q_3} \left( Z^{\frac{1}{M}} - 1 \right), \quad (9)$$

where $$M = \frac{Q_1 + Q_5}{Q_1 + Q_5 - Q_3}. \quad (10)$$

Equations (9) and (10) may be found in U.S. Patent Application Publication No. 2013/0267884, which was incorporated by reference above.

For iso-hematocrit, non-iso-volemic procedures, the time required to reach the target hematocrit ($t_{HF}$) is zero, and equation (9) cannot be used to determine the appropriate replacement fluid and plasma flow rates. Accordingly, the appropriate replacement fluid and plasma flow rates must be determined in a different way.

The time ($t_V$) it takes to achieve a particular change in patient or source blood volume may be expressed as follows:

$$t_V = \frac{\Delta V}{Q_1 + Q_5 - Q_3}, \quad (11)$$

where $\Delta V$ is the target volume change.

In iso-hematocrit, non-iso-volemic procedures according to the present disclosure, the volume ($V_R$) of available replacement fluid is known, with the time ($t_{V_R}$) required to deplete the supply of replacement fluid being expressed as follows:

$$t_{V_R} = \frac{V_R}{Q_1}. \quad (12)$$

The time ($t_{V_R}$) required to deplete the supply of replacement fluid and the time ($t_V$) required to achieve the targeted volume change are equal, because all of the replacement fluid is depleted at the end of the procedure, which is also the time ($t_V$) at which the targeted volume change has been achieved. On account of this relationship, equations (12) and (11) may be equated as follows:

$$\frac{V_R}{Q_1} = \frac{\Delta V}{Q_1 + Q_5 - Q_3}. \quad (13)$$

Equation (13) may be rearranged to isolate the plasma flow rate ($Q_5$) as follows:

$$Q_5 = \left( \frac{\Delta V}{V_R} - 1 \right) Q_1 + Q_3. \quad (14)$$

The replacement fluid flow rate for an iso-hematocrit, non-iso-volemic procedure according to the present disclosure may be calculated by starting with equation (4) and replacing $Q_5$ in equation (4) with equation (14) to arrive at the following equation:

$$H_{T0} = \frac{Q_1}{Q_1 + \left( \left( \frac{\Delta V}{V_R} - 1 \right) Q_1 + Q_3 \right)} H_{T1}. \quad (15)$$

Equation (15) may be rearranged to isolate the hematocrits from the volumes and flow rates as follows:

$$\frac{H_{T0}}{H_{T1}} = \frac{Q_1}{Q_1 \left( 1 + \left( \frac{\Delta V}{V_R} - 1 \right) \right) + Q_3}, \quad (16)$$

which may be simplified to:

$$\frac{H_{T0}}{H_{T1}} = \frac{Q_1}{Q_1 \frac{\Delta V}{V_R} + Q_3}. \tag{17}$$

Finally, rearranging equation (17) to isolate the replacement fluid flow rate ($Q_1$) yields:

$$Q_1 = \frac{H_{T0}}{H_{T1}} \frac{1}{1 - \frac{\Delta V}{V_R} \frac{H_{T0}}{H_{T1}}} Q_3. \tag{18}$$

Thus, equations (14) and (18) may be used by the system controller 138 to calculate proper replacement fluid and plasma flow rates for iso-hematocrit, non-iso-volemic procedures in which the blood draw rate and replacement fluid volume (along with the targeted volume change and the hematocrits of the patient or source's blood and the replacement fluid) are known.

Non-Iso-Hematocrit, Non-Iso-Volemic Procedures

The time ($t_{HF}$) required to achieve a target hematocrit is given by above equation (9), with the time ($t_V$) required to achieve a target volume change being given by above equation (11) and the time ($t_{V_R}$) required to deplete a particular volume of replacement fluid being given by above equation (12). For non-iso-volemic procedures in which the hematocrit of the patient or source's blood is being increased or decreased, these three times ($t_{HF}$, $t_V$, and $t_{V_R}$) may be solved simultaneously to determine the proper replacement fluid flow rate ($Q_1$) and the proper plasma flow rate ($Q_5$).

First, equations (11) and (12) may be equated, as above, to arrive at equation (13). Equation (13) may then be rearranged to yield:

$$Q_1 + Q_5 - Q_3 = \frac{\Delta V}{V_R} Q_1, \tag{19}$$

which may be rearranged to arrive at the following equation:

$$Q_5 - Q_3 = \frac{\Delta V}{V_R} Q_1 - Q_1, \tag{20}$$

which may be simplified to arrive at:

$$Q_5 - Q_3 = \left(\frac{\Delta V}{V_R} - 1\right) Q_1. \tag{21}$$

Rearranging equation (21) to solve for $Q_5$ yields:

$$Q_5 = \left(\frac{\Delta V}{V_R} - 1\right) Q_1 + Q_3. \tag{22}$$

Equation (3) may also be rearranged to solve for $Q_5$:

$$FQ_1 - Q_1 = Q_5 \tag{23}$$

or $$Q_5 = (F-1) Q_1. \tag{24}$$

Equations (24) and (22) may be equated as follows:

$$(F-1) Q_1 = \left(\frac{\Delta V}{V_R} - 1\right) Q_1 + Q_3, \tag{25}$$

which may be rearranged:

$$(F-1) Q_1 - \left(\frac{\Delta V}{V_R} - 1\right) Q_1 = Q_3 \tag{26}$$

and $$\left((F-1) - \left(\frac{\Delta V}{V_R} - 1\right)\right) Q_1 = Q_3 \tag{27}$$

and $$Q_1 = \frac{Q_3}{\left((F-1) - \left(\frac{\Delta V}{V_R} - 1\right)\right)}, \tag{28}$$

which may be simplified to:

$$Q_1 = \frac{Q_3}{F - \frac{\Delta V}{V_R}}. \tag{29}$$

Thus, $Q_1$ and $Q_5$ may be calculated for non-iso-hematocrit, non-iso-volemic procedures by the system controller 138 using equations (29) and (24), respectively, once F has been determined.

The first step of determining F is rearranging equation (21) to solve for $V_R$, as follows:

$$\frac{Q_5 - Q_3}{Q_1} + 1 = \frac{\Delta V}{V_R} \tag{30}$$

and $$V_R = \frac{\Delta V}{\frac{Q_5 - Q_3}{Q_1} + 1}. \tag{31}$$

Next, equations (12) and (9) may be equated because, as noted above, the time ($t_{V_R}$) required to deplete a particular volume of replacement fluid is equal to the time ($t_{HF}$) required to achieve a target hematocrit for non-iso-hematocrit procedures according to the present disclosure in which a supply of replacement fluid is completely depleted. Equating equations (12) and (9) yields:

$$\frac{V_R}{Q_1} = \frac{V_0}{Q_1 + Q_5 - Q_3} \left(Z^{-\frac{1}{M}} - 1\right), \tag{32}$$

which may be rewritten as:

$$\frac{V_R}{Q_1} = \frac{V_0}{(Q_1 + Q_5 - Q_3)}\left[\frac{1}{Z^{\frac{1}{M}}} - 1\right]. \tag{33}$$

Equation (33) may be rearranged to solve for $V_R$ as follows:

$$V_R = \frac{V_0 Q_1}{(Q_1 + Q_5 - Q_3)}\left[\frac{1}{Z^{\frac{1}{M}}} - 1\right], \tag{34}$$

which may be equated with equation (31) to yield:

$$\frac{\Delta V}{\frac{Q_5 - Q_3}{Q_1} + 1} = \frac{V_0 Q_1}{(Q_1 + Q_5 - Q_3)}\left[\frac{1}{Z^{\frac{1}{M}}} - 1\right], \tag{35}$$

which may be rearranged to arrive at:

$$\frac{\Delta V}{V_0} = \left[\frac{1}{Z^{\frac{1}{M}}} - 1\right]. \tag{36}$$

Next, equation (22) is substituted into the denominator of the right side of equation (10) to arrive at:

$$M = \frac{Q_1 + Q_5}{Q_1 + \left(\left(\frac{\Delta V}{V_R} - 1\right)Q_1 + Q_3\right) - Q_3}, \tag{37}$$

which may be simplified to:

$$M = \frac{Q_1 + Q_5}{Q_1} \frac{V_R}{\Delta V}. \tag{38}$$

Substituting equation (3) into equation (38) yields:

$$M = F\frac{V_R}{\Delta V}. \tag{39}$$

Equation (39) may then be substituted into equation (36) to arrive at:

$$\frac{\Delta V}{V_0} = \left[\frac{1}{Z^{F\frac{V_R}{\Delta V}}} - 1\right] \text{ or } \tag{40}$$

$$\frac{\Delta V}{V_0} = \left[\frac{1}{Z^{\frac{V_R F}{\Delta V}}} - 1\right], \tag{41}$$

which may be rearranged to:

$$\frac{\Delta V}{V_0} + 1 = \left[\frac{1}{Z^{\frac{\Delta V}{V_R F}}}\right] \tag{42}$$

and then to:

$$Z^{\frac{\Delta V}{V_R F}} = \left[\frac{1}{\frac{\Delta V}{V_0} + 1}\right]. \tag{43}$$

Equation (2) may then be substituted into equation (43):

$$\left(\frac{H_{T1} - FH_{TF}}{H_{T1} - FH_{T0}}\right)^{\frac{\Delta V}{V_R F}} = \left[\frac{1}{\frac{\Delta V}{V_0} + 1}\right], \tag{44}$$

which may be rearranged to arrive at:

$$\frac{H_{T1} - FH_{TF}}{H_{T1} - FH_{T0}} = \left[\frac{1}{\frac{\Delta V}{V_0} + 1}\right]^{\frac{V_R F}{\Delta V}} \text{ or } \tag{45}$$

$$\frac{H_{T1} - FH_{TF}}{H_{T1} - FH_{T0}} = \left(\frac{1}{1 + \frac{\Delta V}{V_0}}\right)^{\frac{FV_R}{\Delta V}}. \tag{46}$$

With equation (46), and using the Newton-Raphson iteration method, F may be solved for iteratively. In general, the Newton-Raphson method is used to determine the zeroes of a function (i.e., the points at which a plotted curve of the function crosses the x-axis of a Cartesian coordinate system). Initially, a guess or estimate must be made as to the value of a zero of the function, which estimated value may be represented by $F_0$. If $F_0$ is properly chosen, then the Newton-Raphson method may be used to refine the estimated F value using the following iterative equation:

$$F_{n+1} = F_n - \frac{g(F_n)}{g'(F_n)}. \tag{47}$$

Equation (47) effectively solves for the zero or x-axis intercept of a line that is tangential to the plotted curve at the particular $F_n$ value, with the zero or x-axis intercept of the tangent line becoming the next F value ($F_{n+1}$). If $F_0$ is properly chosen (i.e., if it is sufficiently close to an actual zero of the function and it does not represent a point at which a line tangential to the function has no zero or x-axis intercept), each subsequently calculated F value will be closer to the zero of the function than the previous F value (i.e., $F_2$ will be closer to the actual F value than $F_1$, which will be closer to the actual F value than $F_0$). F values may be repeatedly calculated using equation (47) until the difference between consecutive F values is zero or at least sufficiently small (e.g., when consecutive F values are identical to eight decimal points), at which time the last-calculated F value may be considered to be a zero of the function. This F value may then be used in equations (24) and (29) to solve for the proper replacement fluid and plasma flow rates.

In this particular case, equation (46) is first rearranged to solve for the zero crossing of the function:

$$0 = \left(\frac{1}{1+\frac{\Delta V}{V_0}}\right)^{\frac{FV_R}{\Delta V}} - \frac{H_{T1} - FH_{TF}}{H_{T1} - FH_{T0}}, \quad (48)$$

which becomes g(F) in equation (47):

$$g(F) = \left(\frac{1}{1+\frac{\Delta V}{V_0}}\right)^{\frac{FV_R}{\Delta V}} - \frac{H_{T1} - FH_{TF}}{H_{T1} - FH_{T0}}. \quad (49)$$

The derivative of equation (49) is:

$$g'(F) = \frac{V_R \ln\left(\frac{V_0}{\Delta V + V_0}\right)(H_{T1} - FH_{T0})^2 \left(\frac{V_0}{\Delta V + V_0}\right)^{\frac{V_R F}{\Delta V}} + \Delta V H_{T1}(H_{T1} - H_{T0})}{\Delta V (H_{T1} - FH_{T0})^2}. \quad (50)$$

Equations (49) and (50) may be substituted into equation (47), with a first iteration of equation (47) being carried out using a selected $F_0$ value. As noted above, $F_0$ must be properly selected, otherwise the Newton-Raphson method may not be able to determine the actual F value. According to one embodiment of the present disclosure, $F_0$ may be selected by starting with an initial F value $F_i$ of:

$$F_i = \frac{H_{T1}}{H_{TF}}, \quad (51)$$

with the selected $F_i$ value being substituted into equation (49) to determine the value of $g(F_i)$.

If $H_{T1} > H_{TF}$, then $F_i$ may be incrementally increased by a chosen value (e.g., 0.1) until $g(F_i) < 0$, at which point the last $F_i$ value may be used in equations (47), (49), and (50) as $F_0$ to solve for the proper F value. On the other hand, if $H_{T1} < H_{TF}$, then $F_i$ may be incrementally decreased by a chosen value (e.g., 0.1) until $g(F_i) < 0$, at which point the last $F_i$ value may be used in equations (47), (49), and (50) as $F_0$ to solve for the proper F value. With the proper F value, equations (24) and (29) may be used by the system controller 138 to solve for the proper replacement fluid and plasma flow rates.

Non-Iso-Hematocrit, Iso-Volemic Procedures

In iso-volemic procedures, the change in volume of the patient's fluids ($\Delta V$) is zero, which results in division by zero when equations (47), (49), and (50) are used to solve for the proper replacement fluid and plasma flow rates for a non-iso-hematocrit, iso-volemic procedure. However, it has been found that modeling a non-iso-hematocrit, iso-volemic procedure as a non-iso-hematocrit, nominally or marginally non-iso-volemic procedure has been found to be suitable for determining the proper replacement fluid and plasma flow rates. Accordingly, equations (47), (49), and (50) may be used to solve for the proper replacement fluid and plasma flow rates of a non-iso-hematocrit, iso-volemic procedure by providing a non-zero $\Delta V$. Preferably, a nominal or exceeding small $\Delta V$ value (e.g., a $\Delta V$ value of 0.00001) is selected, such that equations (47), (49), and (50) may be used to solve for the proper replacement fluid and plasma flow rates without improperly modeling the procedure as a substantially non-iso-volemic procedure.

Continued Processing

After all of the necessary information has been entered by the operator and the system controller 138 has calculated proper replacement fluid and plasma flow rates, the system controller 138 may carry out the specified procedure. The operator interface module 140 may display different information about the procedure (e.g., the step of the procedure currently being performed, the time and volume of replacement fluid remaining, etc.), while optionally presenting controls that the operator may actuate to modify or otherwise affect the procedure.

In one embodiment, all of the information required to calculate the replacement fluid and/or plasma flow rates may not be available prior to initiation of the procedure, in which case the proper replacement fluid and/or plasma flow rates may be determined during the procedure. For example, the initial hematocrit of the patient or source's blood may not be known at the beginning of the procedure. In this case, the procedure may be initiated using default or entered replacement fluid and/or plasma flow rates, with the hematocrit of the patient or source's blood being determined by monitoring the drawn blood using a sensor or detector or the like. While the procedure continues, the hematocrit of the patient or source's blood is determined, at which time the hematocrit may be entered by the operator using the operator interface module 140 or may be automatically transmitted to the controller 138. With the measured hematocrit information, the controller 138 may calculate the proper replacement fluid and/or plasma flow rates and then modify the operation of the associated pump(s) to bring the replacement fluid and/or plasma flow rates to the proper level(s). In this case, the controller 138 may substitute current values for initial values (e.g., the current available volume of replacement fluid, rather than the initial volume of available replacement fluid) into the appropriate equation(s) when performing the necessary calculation(s).

Even if the proper replacement fluid and plasma flow rates are determined before the procedure is initiated, it is also within the scope of the present disclosure for the system controller 138 to recalculate or update the replacement fluid and/or plasma flow rates during the procedure and modify the operation of the appropriate pump(s), as need be. This may be advantageous in the event of a system disruption or interruption that causes the procedure to stray from the expected performance parameters, such as if a pump rate must be momentarily changed to avoid excess negative pressure in the draw line due to vein-access issues.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system comprising:
a blood separation device configured to separate whole blood from a blood source into a first component including separated red blood cells and a second component including separated plasma;
an inlet pump operable to convey whole blood from the blood source into the blood separation device at a prescribed rate $Q_3$;
a plasma pump operable to convey separated plasma from the blood separation device to the blood source at a plasma flow rate;
a replacement fluid pump operable to convey a replacement fluid to the source at a replacement fluid flow rate; and
a controller programmed to
calculate the plasma flow rate and the replacement fluid flow rate based at least in part on $Q_3$ and a volume $V_R$ of replacement fluid to be flowed to the source,
adjust the operation of the replacement fluid pump to achieve the calculated replacement fluid flow rate, and
adjust the operation of the plasma pump to achieve the calculated plasma flow rate, wherein the plasma flow rate and the replacement fluid flow rate are calculated so as to simultaneously deplete the volume $V_R$ of replacement fluid and achieve one other prescribed process parameter, wherein the prescribed process parameter is one of
maintaining a hematocrit and a fluid volume of the source at constant levels,
maintaining the hematocrit of the source at a constant level while changing the fluid volume of the source from an initial level to a prescribed level,
maintaining the fluid volume of the source at a constant level while changing the hematocrit of the source from an initial level to a prescribed level, and
changing the hematocrit and the fluid volume of the source from initial levels to prescribed levels.

2. The system of claim 1, wherein said one other prescribed process parameter comprises maintaining a hematocrit and a fluid volume of the source at constant levels and the controller is programmed to calculate the plasma flow rate using the following equation:

$$Q_5 = Q_3 - Q_1,$$

where $Q_5$ is the plasma flow rate and $Q_1$ is the replacement fluid flow rate.

3. The system of claim 1, wherein said one other prescribed process parameter comprises maintaining a hematocrit and a fluid volume of the source at constant levels and the controller is programmed to calculate the replacement fluid flow rate using the following equation:

$$Q_1 = \frac{H_{T0}}{H_{T1}} Q_3,$$

where $Q_1$ is the replacement fluid flow rate, $H_{T0}$ is the initial hematocrit of the blood of the source, and $H_{T1}$ is the hematocrit of the replacement fluid.

4. The system of claim 1, wherein said one other prescribed process parameter comprises maintaining the hematocrit of the source at a constant level while changing the fluid volume of the source from an initial level to a prescribed level and the controller is programmed to calculate the plasma flow rate using the following equation:

$$Q_5 = \left(\frac{\Delta V}{V_R} - 1\right) Q_1 + Q_3,$$

where $Q_5$ is the plasma flow rate, $Q_1$ is the replacement fluid flow rate, $\Delta V$ is the difference between the initial fluid volume level of the source and the prescribed fluid volume level of the source, and $V_R$ is the volume of replacement fluid to be flowed to the source.

5. The system of claim 1, wherein said one other prescribed process parameter comprises maintaining the hematocrit of the source at a constant level while changing the fluid volume of the source from an initial level to a prescribed level and the controller is programmed to calculate the replacement fluid flow rate using the following equation:

$$Q_1 = \frac{H_{T0}}{H_{T1}} \frac{1}{1 - \frac{\Delta H_{T0}}{V_R H_{T1}}} Q_3,$$

where $Q_1$ is the replacement fluid flow rate, $H_{T0}$ is the initial hematocrit of the blood of the source, $H_{T1}$ is the hematocrit of the replacement fluid, $\Delta V$ is the difference between the initial fluid volume level of the source and the prescribed fluid volume level of the source, and $V_R$ is the volume of replacement fluid to be flowed to the source.

6. The system of claim 1, wherein said one other prescribed process parameter comprises maintaining the fluid volume of the source at a constant level while changing the hematocrit of the source from an initial level to a prescribed level or changing the hematocrit and the fluid volume of the source from initial levels to prescribed levels and the controller is programmed to calculate the plasma flow rate using the following equation:

$$Q_5 = (F-1) Q_1,$$

where $Q_5$ is the plasma flow rate, $Q_1$ is the replacement fluid flow rate, and the controller is programmed to solve for F using the following iterative equation:

$$F_{n+1} = F_n - \frac{g(F_n)}{g'(F_n)}, \text{ in which}$$

-continued $$g(F) = \left(\frac{1}{1+\frac{\Delta V}{V_0}}\right)^{\frac{FV_R}{\Delta V}} - \frac{H_{T1} - FH_{TF}}{H_{T1} - FH_{T0}}, \text{ and}$$

$$g'(F) = \frac{V_R \ln\left(\frac{V_0}{\Delta V + V_0}\right)(H_{T1} - FH_{T0})^2 \left(\frac{V_o}{\Delta V + V_o}\right)^{\frac{V_R H}{\Delta V}} + \Delta V H_{T1}(H_{T1} - H_{T0})}{\Delta V (H_{T1} - FH_{T0})^2},$$

where $\Delta V$ is the difference between the initial fluid volume level of the source and the prescribed fluid volume level of the source, $V_0$ is the initial fluid volume level of the source, $V_R$ is the volume of replacement fluid to be flowed to the source, $H_{T1}$ is the hematocrit of the replacement fluid, $H_{TF}$ is the prescribed hematocrit level of the source, and $H_{T0}$ is the initial hematocrit of the blood of the source.

7. The system of claim 1, wherein said one other prescribed process parameter comprises maintaining the fluid volume of the source at a constant level while changing the hematocrit of the source from an initial level to a prescribed level or changing the hematocrit and the fluid volume of the source from initial levels to prescribed levels and the controller is programmed to calculate the replacement fluid flow rate using the following equation:

$$Q_1 = \frac{Q_S}{F - \frac{\Delta V}{V_R}},$$

where $Q_1$ is the replacement fluid flow rate, $\Delta V$ is the difference between the initial fluid volume level of the source and the prescribed fluid volume level of the source, $V_R$ is the volume of replacement fluid to be flowed to the source, and the controller is programmed to solve for F using the following iterative equation:

$$F_{n+1} = F_n - \frac{g(F_n)}{g'(F_n)}, \text{ in which}$$

$$g(F) = \left(\frac{1}{1+\frac{\Delta V}{V_0}}\right)^{\frac{FV_R}{\Delta V}} - \frac{H_{T1} - FH_{TF}}{H_{T1} - FH_{T0}}, \text{ and}$$

$$g'(F) = \frac{V_R \ln\left(\frac{V_o}{\Delta V + V_0}\right)(H_{T1} - FH_{To})^2 \left(\frac{V_o}{\Delta V + V_o}\right)^{\frac{V_R H}{\Delta V}} + \Delta V H_{T1}(H_{T1} - H_{T0})}{\Delta V (H_{T1} - FH_{T0})^2},$$

where $V_0$ is the initial fluid volume level of the source, $H_{T1}$ is the hematocrit of the replacement fluid, $H_{TF}$ is the prescribed hematocrit level of the source, and $H_{T0}$ is the initial hematocrit of the blood of the source.

8. The system of claim 7, wherein $\Delta V$ is a nominal, non-zero value when said one other prescribed process parameter comprises maintaining the fluid volume of the source at a constant level while changing the hematocrit of the source from an initial level to a prescribed level.

9. The system of claim 7, wherein the controller is programmed to select $F_0$ for the iterative equation using the following equation:

$$F_i = \frac{H_{T1}}{H_{TF}}$$

and incrementally increasing $F_i$ until $g(F_i) < 0$, with the value of $F_i$ when $g(F_i)$ first equals a value less than zero being selected by the controller to be $F_0$ when $H_{T1} > H_{TF}$.

10. The system of claim 7, wherein the controller is programmed to select $F_0$ for the iterative equation using the following equation:

$$F_i = \frac{H_{T1}}{H_{TF}}$$

and incrementally decreasing $F_i$ until $g(F_i) < 0$, with the value of $F_i$ when $g(F_i)$ first equals a value less than zero being selected by the controller to be $F_0$ when $H_{T1} < H_{TF}$.

11. A method of performing a red blood cell exchange procedure comprising:
    calculating a replacement fluid flow rate and a plasma flow rate;
    drawing whole blood from a source at a prescribed rate $Q_3$;
    separating the whole blood into a first component including separated red blood cells and a second component including separated plasma;
    flowing a replacement fluid to the source at the replacement fluid flow rate; and
    flowing separated plasma to the source at the plasma flow rate, wherein the replacement fluid flow rate and the plasma flow rate are calculated
        based at least in part on $Q_3$ and a volume $V_R$ of replacement fluid to be flowed to the source, and
        so as to simultaneously deplete the volume $V_R$ of replacement fluid and achieve one other prescribed process parameter, wherein the prescribed process parameter is one of
        maintaining a hematocrit and a fluid volume of the source at constant levels,
        maintaining the hematocrit of the source at a constant level while changing the fluid volume of the source from an initial level to a prescribed level, maintaining the fluid volume of the source at a constant level while changing the hematocrit of the source from an initial level to a prescribed level, and changing the hematocrit and the fluid volume of the source from initial levels to prescribed levels.

12. The method of claim 11, wherein said one other prescribed process parameter comprises maintaining a hematocrit and a fluid volume of the source at constant levels and said calculating a replacement fluid flow rate and a plasma flow rate includes calculating the plasma flow rate using the following equation:

$$Q_5 = Q_3 - Q_1,$$

where $Q_5$ is the plasma flow rate and $Q_1$ is the replacement fluid flow rate.

13. The method of claim 11, wherein said one other prescribed process parameter comprises maintaining a hematocrit and a fluid volume of the source at constant levels and said calculating a replacement fluid flow rate and a plasma flow rate includes calculating the replacement fluid flow rate using the following equation:

$$Q_1 = \frac{H_{T0}}{H_{T1}} Q_3,$$

where $Q_1$ is the replacement fluid flow rate, $H_{T0}$ is the initial hematocrit of the blood of the source, and $H_{T1}$ is the hematocrit of the replacement fluid.

14. The method of claim 11, wherein said one other prescribed process parameter comprises maintaining the hematocrit of the source at a constant level while changing the fluid volume of the source from an initial level to a prescribed level and said calculating a replacement fluid flow rate and a plasma flow rate includes calculating the plasma flow rate using the following equation:

$$Q_5 = \left(\frac{\Delta V}{V_R} - 1\right) Q_1 + Q_3,$$

where $Q_5$ is the plasma flow rate, $Q_1$ is the replacement fluid flow rate, $\Delta V$ is the difference between the initial fluid volume level of the source and the prescribed fluid volume level of the source, and $V_R$ is the volume of replacement fluid to be flowed to the source.

15. The method of claim 11, wherein said one other prescribed process parameter comprises maintaining the hematocrit of the source at a constant level while changing the fluid volume of the source from an initial level to a prescribed level and said calculating a replacement fluid flow rate and a plasma flow rate includes calculating the replacement fluid flow rate using the following equation:

$$Q_1 = \frac{H_{T0}}{H_{T1}} \frac{1}{1 - \frac{\Delta V H_{T0}}{V_R H_{T1}}} Q_3,$$

where $Q_1$ is the replacement fluid flow rate, $H_{T0}$ is the initial hematocrit of the blood of the source, $H_{T1}$ is the hematocrit of the replacement fluid, $\Delta V$ is the difference between the initial fluid volume level of the source and the prescribed fluid volume level of the source, and $V_R$ is the volume of replacement fluid to be flowed to the source.

16. The method of claim 11, wherein said one other prescribed process parameter comprises maintaining the fluid volume of the source at a constant level while changing the hematocrit of the source from an initial level to a prescribed level or changing the hematocrit and the fluid volume of the source from initial levels to prescribed levels and said calculating a replacement fluid flow rate and a plasma flow rate includes calculating the plasma flow rate using the following equation:

$$Q_5 = (F-1) Q_1,$$

where $Q_5$ is the plasma flow rate, $Q_1$ is the replacement fluid flow rate, and F is solved for using the following iterative equation:

$$F_{n+1} = F_n - \frac{g(F_n)}{g'(F_n)}, \text{ in which}$$

$$g(F) = \left(\frac{1}{1 + \frac{\Delta V}{V_0}}\right)^{\frac{FV_R}{\Delta V}} - \frac{H_{T1} - FH_{TF}}{H_{T1} - FH_{T0}}, \text{ and}$$

$$g'(F) = \frac{V_R \ln\left(\frac{V_0}{\Delta V + V_0}\right)(H_{T1} - FH_{T0})^2 \left(\frac{V_0}{\Delta V + V_0}\right)^{\frac{V_R H}{\Delta V}} + \Delta V H_{T1}(H_{T1} - H_{T0})}{\Delta V (H_{T1} - FH_{T0})^2},$$

where $\Delta V$ is the difference between the initial fluid volume level of the source and the prescribed fluid volume level of the source, $V_0$ is the initial fluid volume level of the source, $V_R$ is the volume of replacement fluid to be flowed to the source, $H_{T1}$ is the hematocrit of the replacement fluid, $H_{TF}$ is the prescribed hematocrit level of the source, and $H_{T0}$ is the initial hematocrit of the blood of the source.

17. The method of claim 11, wherein said one other prescribed process parameter comprises maintaining the fluid volume of the source at a constant level while changing the hematocrit of the source from an initial level to a prescribed level or changing the hematocrit and the fluid volume of the source from initial levels to prescribed levels and said calculating a replacement fluid flow rate and a plasma flow rate includes calculating the replacement fluid flow rate using the following equation:

$$Q_1 = \frac{Q_5}{F - \frac{\Delta V}{V_R}},$$

where $Q_1$ is the replacement fluid flow rate, $\Delta V$ is the difference between the initial fluid volume level of the source and the prescribed fluid volume level of the source, $V_R$ is the volume of replacement fluid to be flowed to the source, and F is solved for using the following iterative equation:

$$F_{n+1} = F_n - \frac{g(F_n)}{g'(F_n)}, \text{ in which}$$

$$g(F) = \left(\frac{1}{1+\frac{\Delta V}{V_0}}\right)^{\frac{FV_R}{\Delta V}} - \frac{H_{T1} - FH_{TF}}{H_{T1} - FH_{T0}}, \text{ and}$$

$$g'(F) = \frac{V_R \ln\left(\frac{V_0}{\Delta V + V_0}\right)(H_{T1} - FH_{T0})^2 \left(\frac{V_o}{\Delta V + V_o}\right)^{\frac{V_R H}{\Delta V}} + \Delta V H_{T1}(H_{T1} - H_{T0})}{\Delta V (H_{T1} - FH_{T0})^2},$$

where $V_0$ is the initial fluid volume level of the source, $H_{T1}$ is the hematocrit of the replacement fluid, $H_{TF}$ is the prescribed hematocrit level of the source, and $H_{T0}$ is the initial hematocrit of the blood of the source.

18. The method of claim 17, wherein $\Delta V$ is a nominal, non-zero value when said one other prescribed process parameter comprises maintaining the fluid volume of the source at a constant level while changing the hematocrit of the source from an initial level to a prescribed level.

19. The method of claim 17, wherein $F_0$ is selected for the iterative equation using the following equation:

$$F_i = \frac{H_{T1}}{H_{TF}}$$

and incrementally increasing $F_i$ until $g(F_i)<0$, with the value of $F_i$ when $g(F_i)$ first equals a value less than zero being selected to be $F_0$ when $H_{T1}>H_{TF}$.

20. The method of claim 17, wherein $F_0$ is selected for the iterative equation using the following equation:

$$F_i = \frac{H_{T1}}{H_{TF}}$$

and incrementally decreasing $F_i$ until $g(F_i)<0$, with the value of $F_i$ when $g(F_i)$ first equals a value less than zero being selected to be $F_0$ when $H_{T1}<H_{TF}$.

* * * * *